United States Patent [19]
Hurni et al.

[11] 4,319,271
[45] Mar. 9, 1982

[54] AUTOMATED PLATE READER

[75] Inventors: William M. Hurni, North Wales; William J. McAleer, Ambler, both of Pa.

[73] Assignee: Merck & Co. Inc., Rahway, N.J.

[21] Appl. No.: 970,722

[22] Filed: Dec. 18, 1978

[51] Int. Cl.$^3$ .............................................. H04N 7/18
[52] U.S. Cl. ............................. 358/107; 235/92 PC; 358/903; 364/555
[58] Field of Search .................. 235/92 PC; 364/555; 358/107, 903

[56] References Cited

U.S. PATENT DOCUMENTS

| | | | |
|---|---|---|---|
| 3,553,358 | 1/1971 | Lauer | 358/903 |
| 3,773,426 | 11/1973 | Mudd | 356/205 |
| 3,811,036 | 5/1974 | Perry | |
| 4,115,010 | 9/1978 | McAleer | 356/201 |

OTHER PUBLICATIONS

Cox, "Minicomputer Applications in the Virology Laboratory", *International Laboratory*, Mar.–Apr. 1977.

Primary Examiner—Howard Britton
Attorney, Agent, or Firm—Donald J. Perrella; Hesna J. Pfeiffer

[57] ABSTRACT

A method for determining the end point in a viral assay comprising
  electronically scanning a microtiter plate to obtain a plurality of data points from each well,
  transmitting the data points to a digital computer programed to analyze the data points from each well to determine whether each well is positive or negative for CPE in accordance with predetermined parameters, and
  calculating the viral titer from the positive or negative results for each well.

4 Claims, 2 Drawing Figures

AUTOMATED PLATE READER

BACKGROUND OF THE INVENTION

Conventional dilution assays such as bacterial, serological, neutralization and CPE involve determining an effect or lack of an effect in a plurality of wells of a multi-well assay plate. Typically the plate has 96 wells each of which must be inspected separately by a highly skilled individual. This procedure is very time consuming, tedious and expensive. More recently systems have been developed for automated reading of multi-well assay plates, e.g. U.S. Pat. Nos. 3,773,426 and 4,115,010. Such systems operated on the principal of average optical density of each individual well. By recording only an average reading, however, much useful information is lost.

OBJECTS OF THE INVENTION

It is an object of the present invention to provide more sensitive and accurate apparatus and method for automatically determining the dilution end point. Another object is to provide an apparatus and method for automatically determining the dilution end point and automatically recording and processing the data. Still another object is to provide a method and apparatus for automatically determining the dilution end point by use of image analysis techniques. These and other objects of the present invention will be apparent from the following description.

SUMMARY OF THE INVENTION

A method for determining the end point in a viral assay comprising
electronically scanning a multi-well assay plate to obtain a plurality of data points from each well,
transmitting the data points to a digital computer programmed to analyze the data points from each well and to determine in accordance with predetermined parameters whether each well is positive or negative for CPE, and
calculating the viral titer from the positive or negative determination for each well.

DETAILED DESCRIPTION

Figure 1:
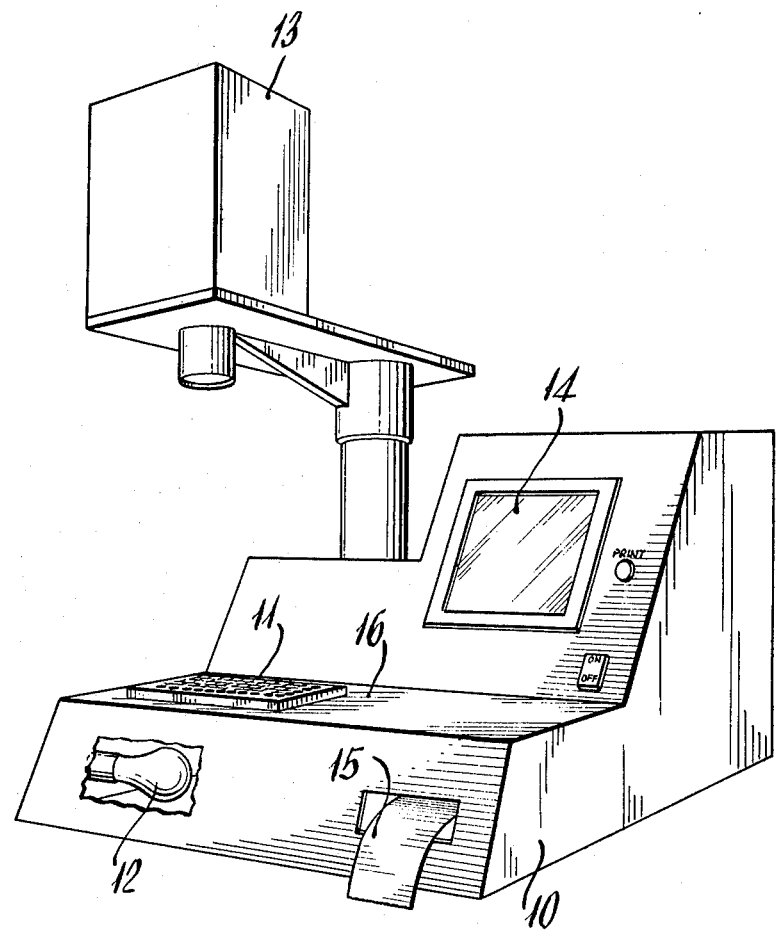
FIG. 1 is a perspective view of apparatus of the present invention.

The method of the present invention is applicable to all dilution assays, one example of which is the CPE (cytopathologic effect) assay.

In the standard cytopathologic effect (CPE) assay, the multi-well assay plate consists of 96 wells comprising 12 separate 8-well dilution assays. Each well contains the same concentration of cells while the concentration of virus diminishes in predetermined ratio in each succeeding well of a particular 8-well assay. In operation the cells and virus are planted in the wells of the multi-well assay plate and incubated for a time sufficient to permit a cell sheet to form and for the virus to act. The wells are then dried, the separate 8-well dilution assays are read and the resultant numbers statistically treated to get the composite viral titer.

It has now been found according to the present invention that the end point of a viral titer can be determined with greater sensitivity and accuracy by electronically determining the CPE for a plurality of points within each well, scoring each point as positive or negative, scoring each well as positive or negative to form a positive-negative matrix, and determining the titer from the matrix using known techniques, e.g., by Reid-Muench calculation.

In contrast to automated plate readers which employ average optical density over each well, the method of the present invention employs electronic scanning techniques, e.g. a television camera, which is capable of visualizing CPE effect in a plurality of discrete areas within each well. The use of electronic scanning means permits the visualizing of CPE effect in many small areas which would be lost when employing techniques operating on the principal of average optical density. When examining a very small area the determination of presence or absence of CPE is much more clear cut and unequivical.

The data points from the scanning are transmitted to a digital computer programmed to score each data point as positive or negative. Once the number of positive and negative data points for a well have been determined, the result is compared to a preset parameter and the entire well is scored positive or negative. When all of the wells in the plate have been scored in this manner, a positive-negative matrix is obtained from which the viral titer is calculated according to known mathematical techniques, e.g. Reid-Meunch calculations.

Referring now to the drawing, the apparatus of the present invention consists of a chassis 10 having a front shelf 16 provided with a slot adapted to receive a multi-well assay plate 11. Light source 12 is provided within the chassis to illuminate the assay plate. While it is convenient that the apparatus of the present invention be provided with its own light source, it is not essential and an independent light source may be utilized. Mounted above the assay plate is a television camera 13 positioned to scan the assay plate and display its image on screen 14. Digital computer means (not shown) are located within the chasis. As the television camera scans each $cm^2$ of surface in each well with about 213 horizontal lines and about 213 vertical lines, approximately 45,000 data points are generated per $cm^2$. As each well in a typical assay plate has an area of about 0.32 $cm^2$, approximately 14,500 data points are generated for each well. The data points from each well of the assay plate are transmitted by the television camera to the computer which is programmed to evaluate each point as positive or negative for CPE, and then to score each well individually as positive or negative. The computer optionally but preferably is further programmed to evaluate the viral titer from the positive-negative matrix which is obtained when each of the wells has been scored. The computer of the apparatus of the present invention can be programmed to print the matrix from which the viral titer may be calculated according to known techniques. Preferably, however, the computer is programmed to calculate and print the viral titer on tape 15. Because the titer is based on such a huge number of points per individual well, rather than on the average optical density, the present invention provides a much more sensitive and accurate determination of viral titer.

Figure 2:
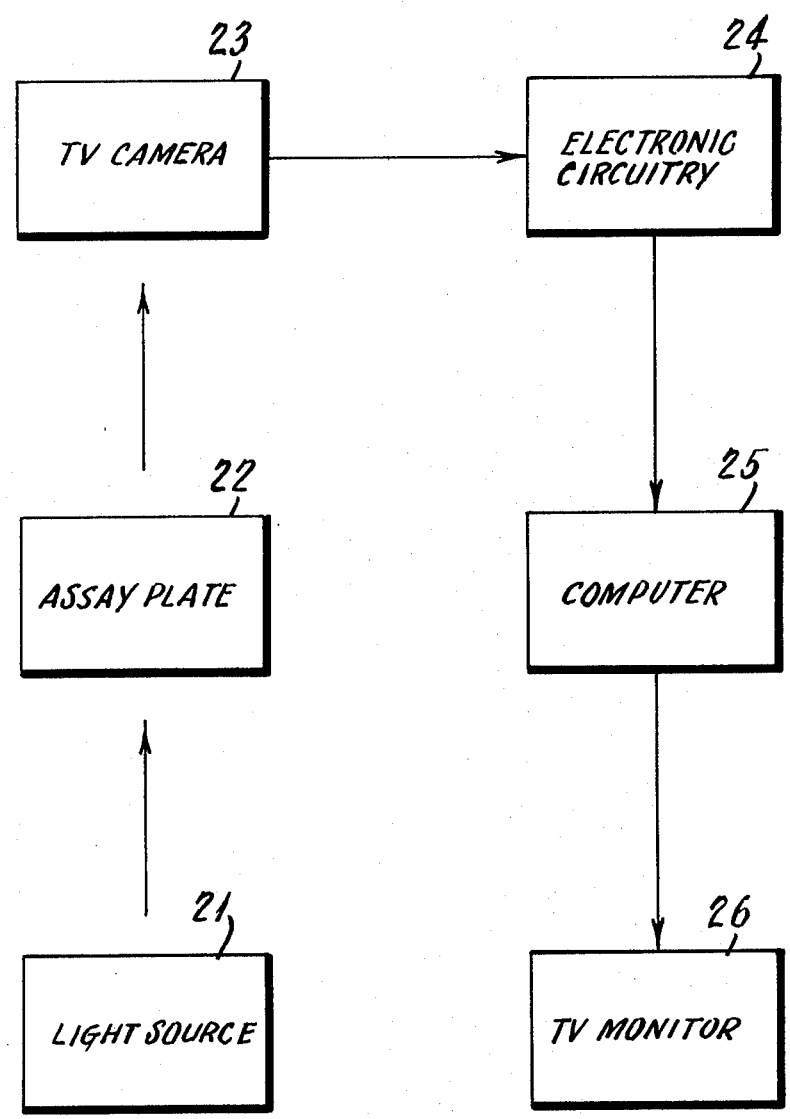
FIG. 2 is a block diagram illustrating the operation of the present invention.

As shown in FIG. 2, light from light source 21 passes through assay plate 22 and is detected by TV camera 23. The electronic circuitry 24 in camera 23 scans each well of assay plate 22 and transmits data points to computer 25 which is programmed to score each well as positive or negative and determines the titer of the virus being assayed. The area scanned by camera 23 is displayed on monitor 26.

The following example illustrates the operation of the apparatus of the present invention.

A microtiter plate each well of which contains a cell sheet free of viral infection is used as a control. This plate is inserted into the slot on the front shelf of the apparatus. The apparatus electronically scans each well in the control plate, determines the number of clear areas in each well, determines the average number of clear areas per well and records the average as the negative control value. A factor of 10% (this value is not fixed but arbitrary) is added to the negative control value and this number is used as the cut off point for scoring a test well positive or negative.

A second microtiter plate having the same type of cell sheet but with virus titrations is then inserted into the slot. Each well in the plate is scanned electronically and the number of clear areas in each well is compared with the cut off value from the control plate. From this comparison each well is scored positive or negative for CPE: positive if above the cut off value and negative if below the cut off value. After a positive-negative matrix has been generated in the microtiter plate, a Reid Meunch calculation is performed by the computer to determine the titer of the plate and thus the titer of the virus being assayed.

What is claimed is:

1. A method for determining viral titer comprising electronically scanning a multi-well assay plate to obtain a plurality of data points from each well, transmitting the data points to a digital computer adapted to analyze the data points from each well and adapted to determine in accordance with predetermined parameters whether each well is positive or negative for cytopathologic effect, and calculating the viral titer from the positive or negative determination for each well.

2. A method according to claim 1 wherein the calculation of viral titer is performed by the computer.

3. A method according to claim 1 where the electronic scanning is at about 213 lines per cm.

4. A method according to claim 1 where the electronic scanning generates about 45,000 data points per $cm^2$ of surface area.